US012514760B2

(12) United States Patent
Buell et al.

(10) Patent No.: US 12,514,760 B2
(45) Date of Patent: Jan. 6, 2026

(54) TAMPON APPLICATOR WITH IMPROVED INSERTION TIP

(71) Applicant: Edgewell Personal Care Brands, LLC, Chesterfield, MO (US)

(72) Inventors: Sezen Buell, Waldwick, NJ (US); Kyle Hillegass, Milltown, NJ (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 0 days.

(21) Appl. No.: 17/693,680

(22) Filed: Mar. 14, 2022

(65) Prior Publication Data

US 2022/0192893 A1 Jun. 23, 2022

Related U.S. Application Data

(63) Continuation of application No. 15/658,125, filed on Jul. 24, 2017, now Pat. No. 11,304,857.

(60) Provisional application No. 62/365,564, filed on Jul. 22, 2016.

(51) Int. Cl.
*A61F 13/26* (2006.01)

(52) U.S. Cl.
CPC .................................. *A61F 13/266* (2013.01)

(58) Field of Classification Search
CPC ....... A61F 13/26; A61F 13/266; A61F 13/263
USPC ....................................... 604/385.17, 358.18
See application file for complete search history.

(56) References Cited

U.S. PATENT DOCUMENTS

| | | | |
|---|---|---|---|
| 3,895,634 A | 7/1975 | Berger et al. | |
| D250,663 S | 12/1978 | Koch et al. | |
| 4,960,417 A | 10/1990 | Tarr, Jr. et al. | |
| 4,973,302 A | 11/1990 | Armour et al. | |
| 5,792,096 A | 8/1998 | Rentmeester et al. | |
| D415,565 S | 10/1999 | Hayes et al. | |
| 6,432,075 B1 * | 8/2002 | Wada | A61F 13/26 604/15 |
| 7,217,252 B2 | 5/2007 | Swick | |
| D572,362 S | 7/2008 | Edgett et al. | |
| D615,202 S | 5/2010 | Edgett et al. | |
| 7,717,873 B2 | 5/2010 | Swick | |

(Continued)

FOREIGN PATENT DOCUMENTS

| | | |
|---|---|---|
| CA | 118802 | 8/2008 |
| CA | 118804 | 8/2008 |

(Continued)

OTHER PUBLICATIONS

International Search report for PCT/US2017/043534, mailed Jan. 4, 2018.

(Continued)

*Primary Examiner* — Catharine L Anderson
*Assistant Examiner* — Meagan Ngo
(74) *Attorney, Agent, or Firm* — Edgar Rodriguez

(57) ABSTRACT

An insertion end for a tampon applicator assembly. The insertion end has an insertion tip region and optionally an inflection region. The insertion end of the tampon applicator assembly is unique in one or more ways, including one or more of the following: having a unique degree of closure, an inflection region length that is different than an insertion end region length, petal slits that form a tear-drop shape, petals having multiple radii of curvature, the insertion end having a unique radius of curvature, the insertion end having a unique part thickness.

12 Claims, 8 Drawing Sheets

(56) References Cited

U.S. PATENT DOCUMENTS

| | | | |
|---|---|---|---|
| 7,727,208 | B2 | 6/2010 | Lemay et al. |
| D626,650 | S | 11/2010 | Edgett et al. |
| 8,162,872 | B2 | 4/2012 | Loyd et al. |
| D664,656 | S | 7/2012 | Avigdor et al. |
| D665,499 | S | 8/2012 | Avigdor et al. |
| 9,339,419 | B2 | 5/2016 | VanDenBogart et al. |
| 9,510,978 | B2 | 12/2016 | Nellenbach et al. |
| 9,532,907 | B1 | 1/2017 | Agrawal |
| 2004/0064082 | A1 | 4/2004 | LeMay et al. |
| 2004/0243088 | A1 | 12/2004 | LeMay et al. |
| 2006/0173400 | A1 | 8/2006 | Suga et al. |
| 2007/0156080 | A1 | 7/2007 | Loyd et al. |
| 2007/0167902 | A1* | 7/2007 | Edgett .................. A61F 13/266 604/15 |
| 2010/0016780 | A1 | 1/2010 | VanDenBogart et al. |
| 2010/0324468 | A1 | 12/2010 | Gann et al. |
| 2011/0152742 | A1 | 6/2011 | Cardinahl et al. |
| 2011/0201992 | A1 | 8/2011 | Smet et al. |
| 2011/0273727 | A1* | 11/2011 | Seki .................... A61F 13/2051 33/700 |
| 2012/0204410 | A1* | 8/2012 | Mastalish ............... A61F 13/26 29/505 |
| 2014/0155808 | A1* | 6/2014 | Nellenbach ........... A61F 13/266 604/14 |
| 2014/0257777 | A1* | 9/2014 | Li .......................... G06F 30/20 703/6 |
| 2015/0105711 | A1* | 4/2015 | LeMay ................. A61F 13/266 604/15 |

FOREIGN PATENT DOCUMENTS

| | | | |
|---|---|---|---|
| EM | 000643028-0002 | | 12/2006 |
| EM | 000643028-0003 | | 12/2016 |
| EM | 000643028-0004 | | 12/2016 |
| EM | 000643028-0005 | | 12/2016 |
| EM | 000643028-0006 | | 12/2016 |
| EM | 000643028-0007 | | 12/2016 |
| EM | 000643028-0008 | | 12/2016 |
| EM | 000643028-0009 | | 12/2016 |
| EP | 000643028-0001 | | 12/2006 |
| EP | 000643028-0010 | | 12/2006 |
| EP | 000643028-0011 | | 12/2006 |
| JP | 2001-145658 | A | 5/2001 |
| JP | 2016-500023 | A | 1/2016 |
| MX | 25426 | | 12/2006 |
| MX | 25750 | | 12/2006 |

OTHER PUBLICATIONS

Unofficial translation of Japanese Office Action issued in connection with JP Application No. 2018-545947 dated Apr. 26, 2021.
Non-Final Rejection from U.S. Appl. No. 15/658,125 dated Sep. 18, 2019.
Non-Final Rejection from U.S. Appl. No. 15/658,125 dated Apr. 29, 2020.
Final Rejection from U.S. Appl. No. 15/658,125 dated Aug. 28, 2020.
Non-Final Rejection from U.S. Appl. No. 15/658,125 dated Apr. 6, 2021.
Final Rejection from U.S. Appl. No. 15/658,125 dated Aug. 17, 2021.
International Preliminary Report on Patentability for PCT/US2017/043534, dated Jan. 22, 2019.
Unofficial translation of Japanese Office Action issued in connection with JP Application No. 2018-545947 dated Aug. 30, 2022.
Office action dispatched Jan. 4, 2024 in Japanese Patent Application No. 2023-068648.
Unofficial translation of office action issued in Japanese Patent Application No. 2023-068648 on Jul. 23, 2024.
Unofficial translation of Decision of Rejection issued in Japanese Patent Application No. 2023-068648 on Mar. 24, 2025.

* cited by examiner

TAMPON APPLICATOR WITH IMPROVED INSERTION TIP

CROSS-REFERENCE TO RELATED APPLICATIONS

This application is a continuation of U.S. patent application Ser. No. 15/658,125, filed Jul. 24, 2017, which claims priority to U.S. Provisional Patent Application No. 62/365,564, filed Jul. 22, 2016, the disclosure of which is hereby incorporated by reference in its entirety.

The present disclosure relates to a tapered tampon applicator with an improved insertion tip that allows for increased comfort and confidence in use.

BACKGROUND

Commercial tampon applicators are typically formed from two components, namely a barrel, in which an absorbent pledget is held, and a plunger. The barrel has an insertion end that may be blunt and open-ended, but is often rounded, e.g., dome-shaped, and typically includes a number of petals that open when the pledget is forced against them during ejection. A tapered insertion end lends itself to greater ease of insertion and insertion comfort to a user, as opposed to the blunt, open-ended design.

U.S. Pat. No. 8,444,590 discloses a tampon applicator having a plunger and a barrel having a tapered insertion tip providing enhanced insertion comfort, as opposed to a generally spherical tip. The taper of the insertion tip is defined by a ratio of the length of the taper projection along a longitudinal axis of the barrel to the length of the taper projection along a radius of the barrel at a base region of the insertion tip. The insertion end of the barrel comprises two or more petals, preferably with a substantially uniform thickness. Through both qualitative and quantitative consumer research, it has been shown that providing a tapered insertion tip greatly enhances the actual and perceived level of comfort associated with inserting a tampon applicator. The tampon applicator can be prepared from a variety of materials including cardboard and thermoplastic polymers.

It is further disclosed in U.S. Pat. No. 8,444,590 that the thickness of the petals influences two key factors of tampon performance, ejection force, i.e., the amount of force the user applies to the plunger to eject the pledget from the applicator, and petal tip stability. In general, an ejection force of greater than 25 oz is unacceptable to the consumer and an ejection force of less than 20 oz is typically preferred. If the petal tips are unstable, they may open, collapse or otherwise deform, which may render the tampon uncomfortable to use or even unusable. The thickness of the applicator petals can be altered to influence the ejection force and/or petal stability of the applicator. Thin petals, especially those below about 0.022 inches in thickness, tend to lower the ejection force, and decreasing petal thickness further may further lower ejection force.

On the other hand, if the applicator material is not stiff or rigid enough, the thinner petals may experience tip stability problems, or may collapse inward upon insertion. The petals of U.S. Pat. No. 8,444,590 have a thickness of about 0.004 inches to about 0.022 inches, preferably, about 0.008 inches to about 0.018 inches, and more preferably, about 0.009 inches to about 0.013 inches. It is disclosed that increasing the petal thickness to greater than about 0.025 inches can help increase the petal stability and/or collapse issue, however this increases ejection force.

U.S. Pat. No. 8,162,872, discloses a tampon applicator wherein the insertion tip comprises 4 to 6 petals, which petals are separated from each other by slits that are non-linear and not parallel with the longitudinal axis of the barrel. Linear slits separating the petals are common in many commercial applicators. As discussed in U.S. Pat. No. 8,162,872, petals of the insertion tip are designed to be thin and flexible to open with minimal force so that the petals do not provide a large resistance that makes it difficult to eject the tampon from the tampon applicator.

As noted in U.S. Pat. No. 8,444,590, petals are often designed to be "weaker" than the rest of the applicator for this reason. However, as pointed out in U.S. Pat. No. 8,162,872, overly weak petals have a potential to cause injury during insertion, and some users complain that such petals result in pinching when the petals close after the tampon is expelled from the applicator. It is further noted in U.S. Pat. No. 8,162,872 that weaker petals are more likely to bend and thus disrupt the surface of the generally domed shape, possibly leading to scratching or other injury during insertion of the tampon applicator into the vagina or removal from the vagina after expulsion of the tampon.

U.S. Pat. No. 9,192,522 discloses a tampon applicator assembly having an applicator barrel with a tapered insertion tip similar to that of U.S. Pat. No. 8,444,590, which applicator assembly is provided with a shaped pledget, e.g., shaped in a manner similar to the shape of the end of the barrel that includes the injection tip. The shaped pledget, can thus be housed at least partially within the insertion tip to support the petals and help prevent deformation of thin, very flexible petals that can lead to scratching, pinching, etc.

While the shaped, petal supporting pledget of U.S. Pat. No. 9,192,522 can improve the comfort for the end user and increase confidence when using an applicator with a tapered insertion tip, and very thin, flexible petals, further improvements are still needed, both from the point of view of the consumer and from the point of view of the manufacturer.

In addition to the possible harm to the user caused by overly weak petals, efficient large scale production of articles with very thin sections can be quite demanding. For example, many tampon applicators are prepared by molding thermoplastic polymers, such as polyolefins, or blends of thermoplastics with elastomers. Many polymer compositions capable of providing the functional and aesthetic properties desired for a tampon applicator, i.e., flexibility, lubricity, smoothness, consistent color etc., can produce excessive waste when using certain molding techniques due to rupture, tearing or other damage of the article. This can be particularly problematic at sections of the article that are delicate, e.g., thin walled petals, or subjected to high stress during processing, e.g. points where the slits defining the petal meet the main body of the barrel.

The conceptually simple expedient of preparing a more structurally robust applicator by incorporating thicker petals, or petals formed slightly stiffer polymer compositions, could allow for more efficient or flexible manufacturing processes, while also providing an applicator less likely to cause discomfort upon insertion or withdrawal. However, as discussed in the art above, incorporating this change directly into the presently configured tampon applicators is likely to increase the ejection force needed to operate the applicator beyond what is acceptable to the end user.

A tampon applicator with a reconfigured tapered insertion tip that can overcome issues related to end user comfort while operating with an acceptably low ejection force is highly desirable. Typically, an ejection force between 5 and 25 oz. is desired and an ejection force between 10 and 20 oz.

is generally preferred. It has been found that providing a wider closure at the terminus of the insertion tip, and/or extending the length of the petals can reduce the force required to eject a pledget from the applicator. Making these changes to the architecture of presently sold tampon applicators, even to a small degree, can lead to noticeable improvements in utility and comfort, and may also permit other changes in the design and construction of applicators, such as the use of thicker or more robust petals, that provide additional improvements to both the end user and the manufacturer.

Aside from providing a user-friendly product in, inter aha, comfort and ejection force, manufacturing such products can be equally as challenging. Costs of materials fluctuate, as does the availability of certain preferred materials. Furthermore, tooling to support new products having improved characteristics can be costly and present challenges on top of material sourcing challenges. Suffice it to say, having a flexible product strategy that enables a manufacturer multiple levers or options to choose from while still yielding a further unique, favorable and/or improved consumer product is desirous.

SUMMARY

A tampon applicator assembly is provided, including a tampon applicator and a tampon pledget. The tampon pledget has an insertion end and a rearward end. The rearward end typically includes a withdrawal string. The insertion end is optionally tapered.

The tampon applicator assembly defines a straight central and longitudinal axis running axially along its length. The tampon applicator is substantially straight along this central longitudinal axis—the components of the applicator are coaxial about the straight central longitudinal axis. The tampon applicator includes a barrel and a plunger. The plunger is a single piece or is optionally a two-piece plunger. In either configuration, the plunger telescopically engages the tampon pledget housed within the barrel, or said differently, the plunger telescopically engages the barrel and applies force to the rear end of the tampon pledget. In configurations having a two-piece plunger, the plunger segments (i.e., inner segment) telescopes within the other plunger segment (i.e. the outer plunger) to provide a shorter applicator footprint in a non-use or storage state.

The barrel includes an insertion end, a main body region, and a reverse taper region, and/or a grip region. The insertion end includes an insertion tip region and optionally an inflection region. The insertion tip region and inflection region are distinct, overlap, or coincide. In any embodiment, the insertion tip region defines the length of the petals (i.e. the length of the free end of the petal to the base where the slit separating the petals terminate). While the inflection region defines the length that corresponds to the inflection curvature of the insertion end of the barrel. The applicator has between 3 and 8 petals that define the insertion end.

The insertion end via the petals defines a closure geometry, or said differently, defines the amount of space between the free petal ends. The closure geometry is defined by the inscribed shape amongst the petal tips, which is typically a polygonal shape. For instance, if the insertion end has four petals, the inscribed polygon might resemble a quadrilateral. The closure geometry (defining a polygon) further defines a circle inscribed within the polygon. The diameter of the circle is between about 0.075 inches and about 0.150 inches.

The circular or elliptical insertion tip opening (i.e. as defined by a slice along the longitudinal axis of the applicator) is defined by a circle or ellipse inscribed within a regular polygon wherein the termini (i.e. free ends) of the petals represent the midpoint or an end point of each side of the polygon. For example, for a barrel having a generally circular interior region and an insertion end defined by four petals, the insertion end opening is the circle inscribed within the square wherein the terminus of a petal represents the midpoint of each side of the square. In embodiments having five petals, the insertion tips define endpoints of a pentagon, and a circle is inscribed within the pentagon such that the circle touches the midpoints of each side of the pentagon.

The degree of closure is defined as a ratio of the inscribed circle as defined by the free end of the petals to the cross-section of the base region of the petals. Said differently, the degree of closure is the ratio of the diameter of the insertion end opening to a corresponding diameter of the hollow interior of the main body in the region where the insertion tip adjoins the main body. This ratio is compares the relative diameters of the inscribed circles. The degree of closure is between about 0.1 and about 0.3, or between about 0.1 to about 0.25, or about 0.12 to about 0.20, or about 0.14 to about 0.20.

For example, for a tampon applicator barrel having a generally circular interior region and a generally circular insertion tip opening, the degree of closure is the ratio of the diameter of the insertion tip opening to the diameter of the interior of the barrel where the insertion tip adjoins the main body. For example, a degree of closure of 0.1 means that the insertion tip opening is one-tenth the size of the barrel interior at the point in the region where the insertion tip adjoins the main body. In the case of a circular opening defined by an even number of petals, this is also the distance between the termini of two opposing petals.

As described above, the insertion tip region and the inflection region are distinct, overlap or coincide. As such, the insertion tip region and/or the inflection region has a taper ratio exceeding about 1.0, or from about 1.3 to about 3.5, e.g., about 1.3 to about 2.5, about 1.5 to about 2.5, or about 1.7 to about 2.3, or about 1.6 to about 2.2. The taper ratio is defined by the formed applicator (i.e. the petals are formed into a curved shape).

The formed length of the insertion tip region is thus the axial length between the formed free petal ends and where the slits (or cuts) separating the petals from each other terminate. The insertion tip taper ratio is the ratio between the formed insertion tip region length and the radius of the barrel where the slits separating the petals terminate. The insertion tip taper ratio is greater than about 1.0.

The formed length of the inflection region is the length between where the insertion curvature ends and where the cuts separating the petals from each other terminate. In some embodiments, the inflection taper ratio is the ratio of (a) the sum of the formed insertion tip region length and the formed inflection region length to (b) the larger of the radius of the barrel where the insertion curvature ends and the radius where the slits between the petals terminate. The inflection taper ratio is greater than about 1.0.

The formed length of the insertion tip region does not equal the formed length of the inflection region. In some embodiments, the formed length of the insertion tip region is greater than the formed length of the inflection region. In other embodiments, the formed length of the insertion tip region is less than the formed length of the inflection region. The insertion tip region length is different from the inflection region length. The main body region has a taper that is distinct from the insertion tip region and/or the inflection region. In some embodiments, the main body region is substantially straight-walled such that it does not have a taper. In some embodiments, the main body region has a linear taper while the insertion curvature is non-linear. In some embodiments, the insertion curvature is different from the curvature of the main body region taper. As discussed herein, the insertion curve, in some embodiments, has multiple radii of curvature. In some such embodiments, the radii of curvature adjacent the main body region has a different radii of curvature than the main body region. In other such embodiments, the insertion curvature defines a general curvature equation that is distinct from the taper equation defined by the main body region. As such, in embodiments where the main body region is not substantially straight, one skilled in the art is able to discern where the insertion curvature ends and the main body region begins.

Also provided is a tampon assembly comprising the tampon applicator of the present disclosure and an absorbent pledget held within the applicator barrel, wherein a force of from about 5 to about 25 ounces, i.e., about 1.4 to about 6.9 Newton (N), is required to eject the pledget, for example from about 8 to about 20 oz, i.e., 2.2 to 5.6 N, e.g., about 10 to about 20 oz, i.e., 2.8 to 5.8 N, about 10 to about 15 oz, i.e., 2.8 to 4.2 N, or about 10 to about 12 oz, i.e., 2.8 to 3.3N, is required to eject the pledget.

In the case of an elliptical barrel and elliptical insertion tip opening, the ratio is determined by the widths of corresponding parts of the barrel interior and the insertion tip opening, e.g., the widest length in each or the narrowest length in each.

The taper ratio of the insertion tip is defined by the ratio of the length of the taper projection along the longitudinal axis of the barrel to the length of the taper projection along a radius of the barrel at a base region of the insertion tip, i.e., the region where the insertion tip region (and/or the inflection region) adjoins the main body of the barrel. In the case of a generally circular barrel, this translates to ratio of the length of the insertion tip to the radius of the circle described by the exterior of the barrel at the base of the insertion tip. In the present disclosure, the taper ratio of an elliptical barrel is the ratio of the length of the insertion tip to the radius at the widest part of the barrel at the base of the insertion tip.

In some cases, the degree to which enlarging the insertion tip opening or increasing the total petal length will depend to some extent on the shape of the petal. The petals of the present disclosure, in an unformed (i.e. straight) state, have a generally triangular, semi-circular, parabolic, elliptical and/or hyperbolic shape, and in some embodiments a portion of the petal, e.g., near the base of the petal, has a generally linear shape. In some embodiments of the present disclosure it is found that providing a rounder or further blunt petal terminus, a longer linear region, or a less steep parabolic curve can have an effect on the ejection force, and in some embodiments, the adjustments are made to the design of the petal to account for these interactions. In other embodiments, two adjacent petals converge at the barrel region (i.e. at the base of the petals) to form a tear drop shape. In further embodiments, the one or more petals have more than one radius of curvature such that at least one of the one or more radii have a generally parabolic, hyperbolic and/or elliptical shape. In some embodiments, the petal has at least two radii of curvature, at least three radii of curvature, or at least four radii of curvature.

The applicator of the present disclosure thus has an improved tapered insertion tip configuration that provides the comfort associated with tapered applicators, which configuration also lowers the applicator ejection force. By using a configuration with a lower ejection force, other changes to the design and composition are possible that can further improve the applicator, for example, the need for extremely thin or weak petals is diminished, which can lead to less deformation of the tip and greater comfort in use.

Figure 7:
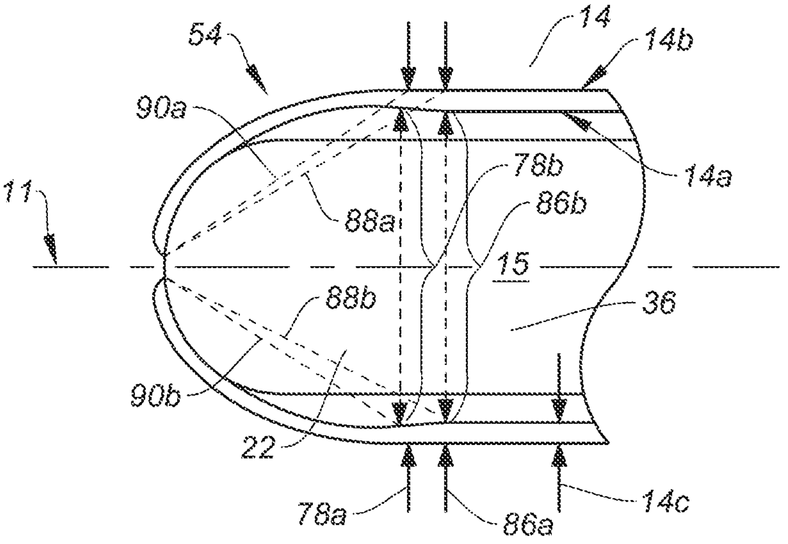
Figure 8:
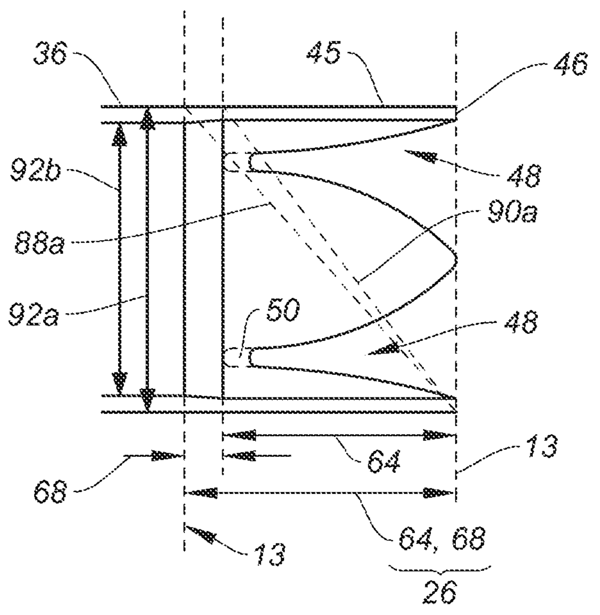
Figure 9:
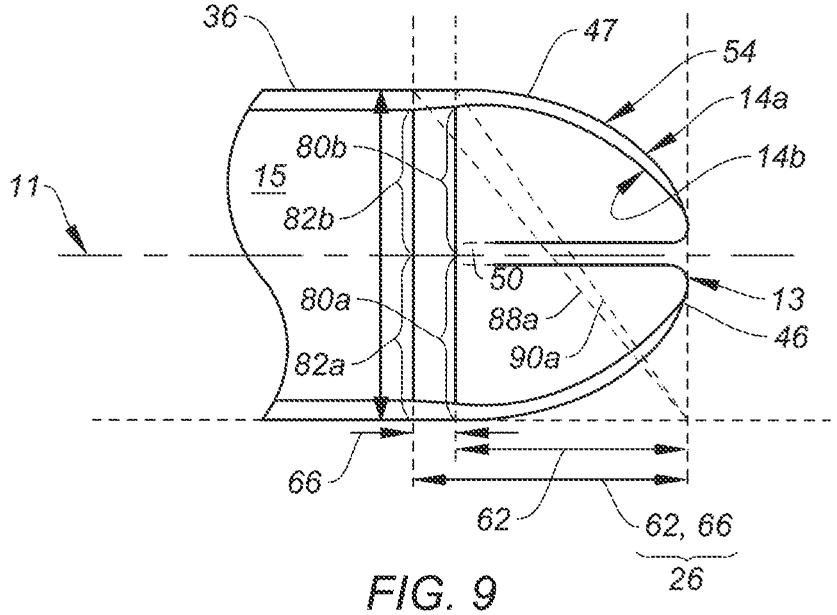
Figure 10:
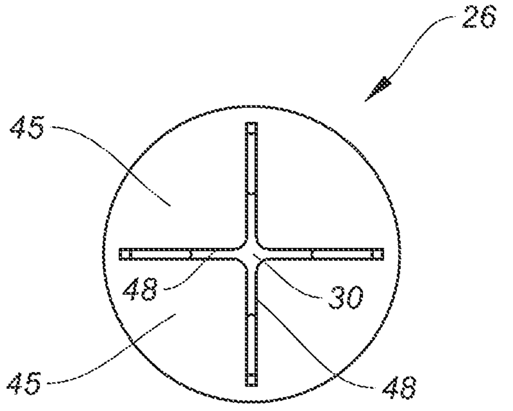
Figure 11:
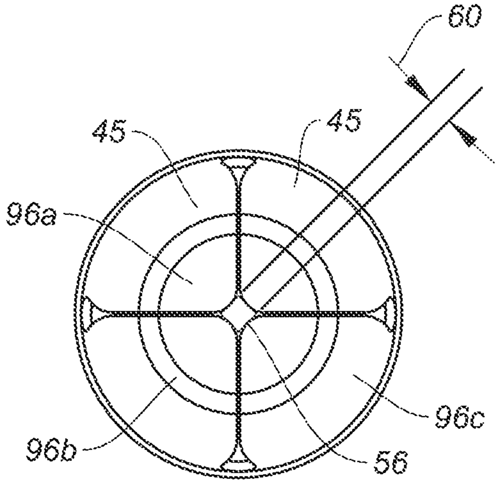
Figure 12:
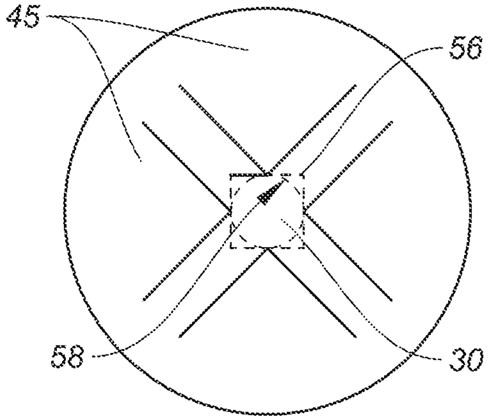
Figure 13:
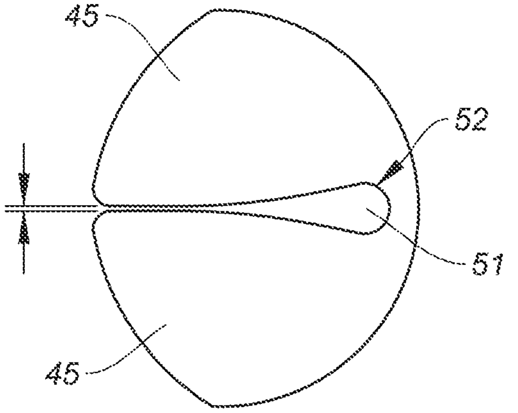
Figure 14:
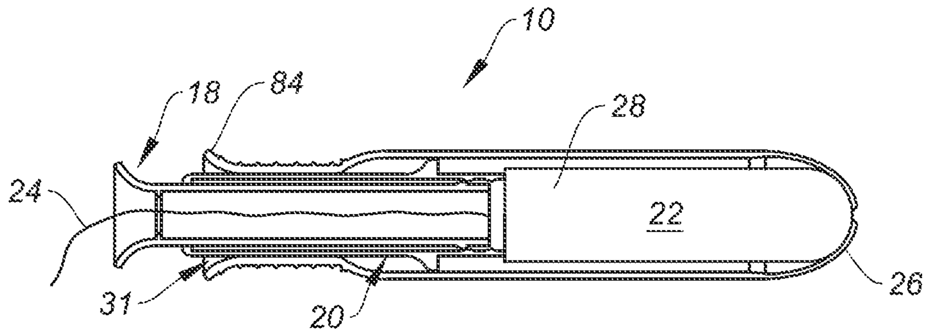
Figure 15:
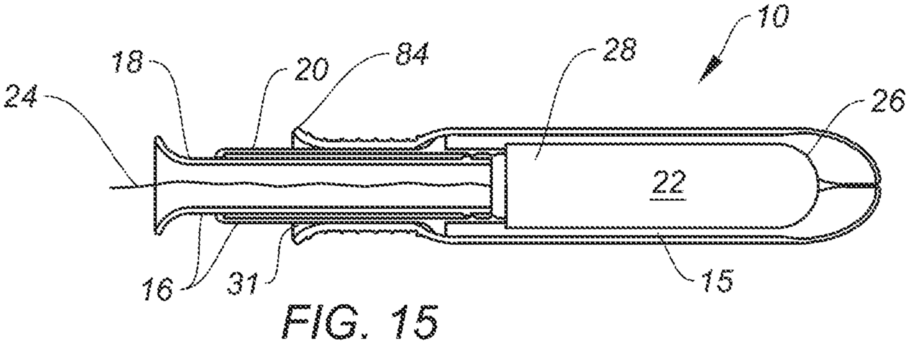
Figure 16:
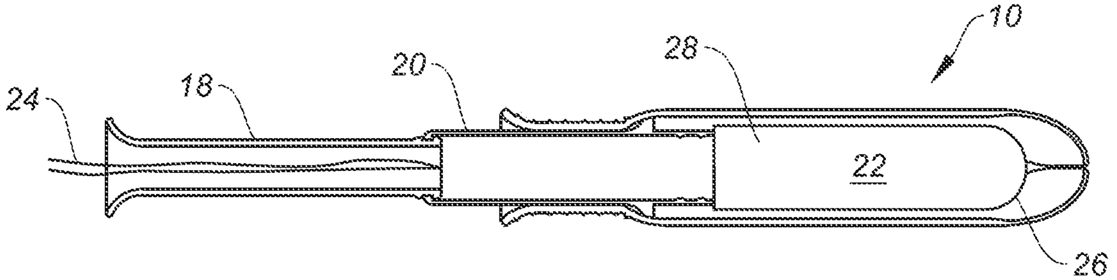
Figure 17:
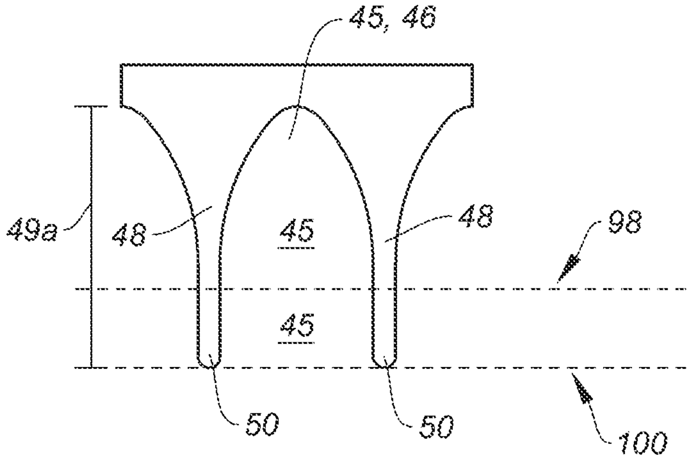
Figure 18:
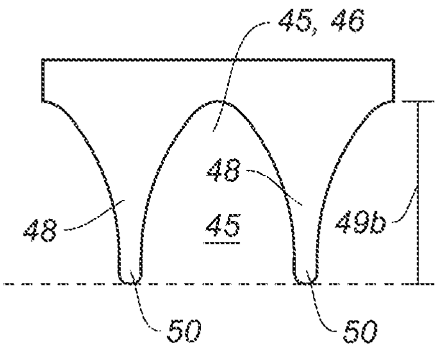
Figure 19:
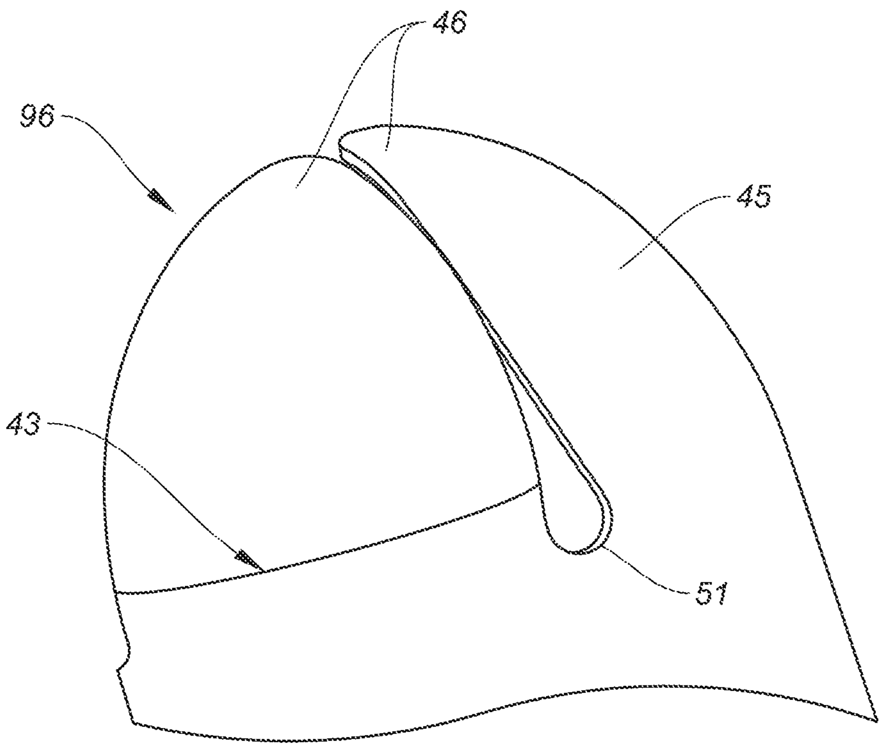
Figure 20:
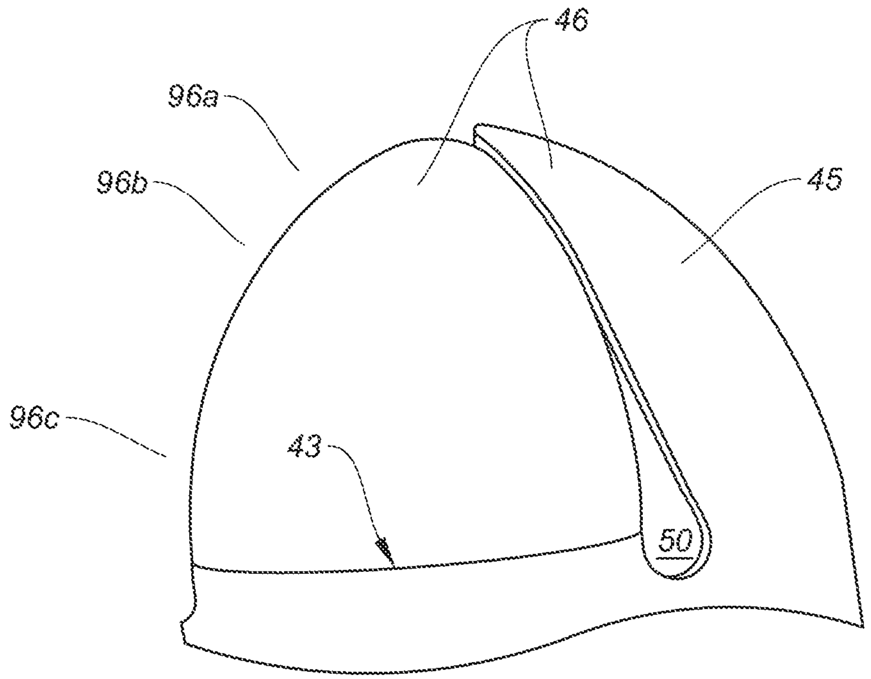

FIG. *6a-6c* is a schematic representation of a cross-sectional view of an applicator insertion tip and inflection region;

FIG. 7 is a schematic representation of a cross-sectional view of an applicator insertion tip and inflection region;

FIG. 8 is a schematic representation of a cross-sectional view of an applicator insertion tip and inflection region;

FIG. 9 is a schematic representation of a cross-sectional view of an applicator insertion tip and inflection region;

FIG. 10 is a front view of an applicator insertion tip and inflection region;

FIG. 11 is a front view of an applicator insertion tip and inflection region;

FIG. 12 is a front view of an applicator insertion tip and inflection region;

FIG. 13 is detailed view of an insertion tip and inflection region;

FIG. 14 is a diagrammatic sectional view of a compact applicator assembly in a compact or storage configuration;

FIG. 15 is a diagrammatic sectional view of a compact applicator assembly in an extended or prepped configuration;

FIG. 16 is a diagrammatic sectional view of a compact applicator assembly wherein the pledget has been ejected from the applicator;

FIG. 17 is a diagrammatic view of a petal configuration;

FIG. 18 is a diagrammatic view of a petal configuration;

FIG. 19 is an angled partial view of an insertion tip and inflection region; and FIG. 20 is an angled partial view of an insertion tip and inflection region.

DETAILED DESCRIPTION

The tampon applicator assembly 10 of the present disclosure has many general features in common with tampon applicators known in the art, i.e., a plunger 16 and a barrel 14 being generally tubular in shape defining a hollow cavity 15 and having two opposing ends 44, 84—a forward most end 44 and a rearward most end 84—wherein each end 44, 84 comprises an opening. The barrel 14 includes one or more of an insertion end 26, a main body region 36, and a reverse taper region 38, a grip region 40. The main body region 36 has a length 72, the finger grip region 40 has a length 74, and the reverse taper region 38 has a length 76. The tampon applicator 12 has a plunger 16 slideably disposed in the hollow cavity 15 and the rearward most end 84. The forward most end 44 has an insertion end 26. The insertion end 26 includes a plurality of petals 45. The petals 45 are initially in an unformed or straight position, and after assembly of the tampon applicator assembly 10 is sufficiently completed (i.e. at least the tampon pledget 22 is inside the hollow cavity 15, as shown at least in FIG. 7), the insertion end 26 is closed or formed. The insertion end 26 opens when the pledget 22 housed in the barrel 14 is forced (via pressure exerted by the plunger 16) against the petals 45, making the forward most end 44 of the insertion end 44 opening 30 larger, through which larger opening 30 the pledget 22 is ejected. The pledget has a withdrawal end 28 and includes a withdrawal string 24.

Figure 1:
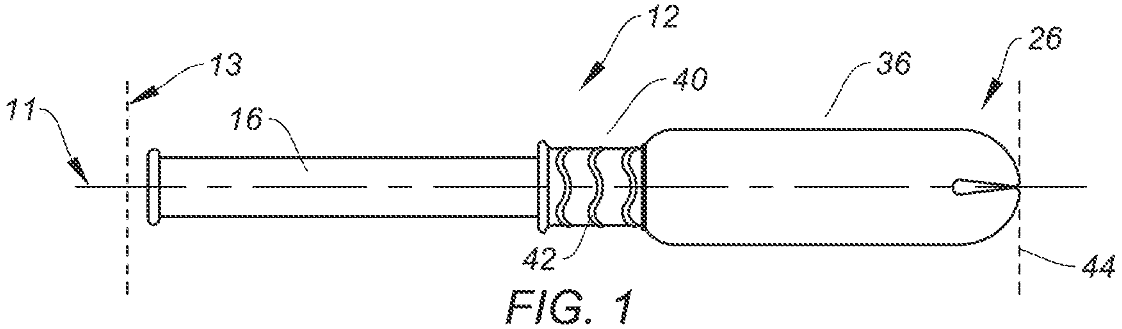
FIG. 1 shows a tampon applicator with a rounded or dome-shaped insertion tip.

The tampon applicator 12 is a full-sized applicator 12 having a full-size barrel 14 and optionally a single piece plunger 16 as shown in FIG. 1 and/or a compact applicator as shown in FIGS. 14-16. Compact applicators can have a single piece plunger (not shown in FIGS. 14-16) and/or a two-piece plunger 16 as shown in FIGS. 14-16. A two-piece plunger includes an inner plunger 18 and an outer plunger 20, such that the inner plunger 18 telescopically engages outer plunger 20. Both inner plunger 18 and outer plunger 20 telescopically engage the barrel 14 when in a connected/extended configuration. Optionally, compact applicators can have a full-size barrel 14, as shown in FIGS. 2-5. The tampon applicator 12 can be made from a variety of materials including cardboard, thermoplastic, and/or elastomeric polymers, and the applicator 12 may also be coated by materials that may further aid in the comfort or utility of the applicator 12.

For example, FIG. 1 shows a familiar tampon applicator 12, with the plunger 16, and a barrel 14 comprising a textured finger grip region, a main body region 36, and an insertion end 26. In FIG. 1 the plunger enters the barrel 14 through the finger grip region 40.

To improve insertion ease of the applicator 12, the architecture of the insertion end 26 has been reconfigured. Prior to operation of the applicator 12 but after assembly of the tampon applicator assembly components, the insertion end 26 has a defined taper, length, and closure. Such characteristics are determined by the shape and length of the individual petals 45 and/or the inflection curvature 54. Differences between the tampon applicator 12 of the present disclosure and the prior art can include one or more of the introduction of a unique or larger degree of closure at the forward most end 44 of the insertion end 26, lengthening of the petals 45 that form the insertion end 26 or lengthening the inflection curvature 54, having a unique petal gap 51, and/or the use of differently shaped petals 45 (i.e. curvature, width, thickness). As for the latter, differently shaped petals include petals 45 having different or multiple radii of curvature, having different shaped slits 48, having slits 48 with distinct radii of curvature. In such embodiments, the shape of the petals 45 leads to a unique inflection curvature 54, and/or an insertion end 26 having multiple radii of curvature.

The insertion end 26 includes an insertion tip region 32 and optionally an inflection region 34. The insertion tip region 32 and inflection region 34 are distinct, overlap, or coincide. In any embodiment, the insertion tip region 32 defines the length 62 of the formed petals 45 (i.e. the length of the free end 46 of the petal 45 to the base where the slits 48 separating the petals 45 terminate 50). While the inflection region 34 defines the length 66 (i.e. the inflection region length 66) that corresponds to the inflection curvature 54 of the insertion end 26. The applicator 12 has between 3 and 8 petals 45 that define the insertion end 26.

The insertion end 26 via the petals 45 defines a closure geometry, or said differently, defines the amount of space between the free petal ends 46. The closure geometry is defined by the inscribed shape 56 amongst the free petal ends 46 (i.e. petal tips), which is typically a polygonal shape. For instance, if the insertion end 26 has four petals 45, the inscribed polygon 56 might resemble a quadrilateral. The closure geometry (defining a polygon) further defines a circle 58 inscribed within the polygon 56. The diameter 60 of the circle 58 is between about 0.075 inches and about 0.150 inches.

Figure 2:
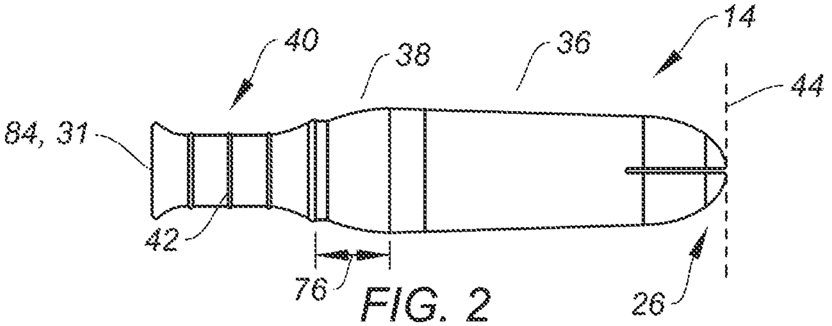
FIG. 2 shows a tampon applicator with a tapered insertion tip.
Figure 3:
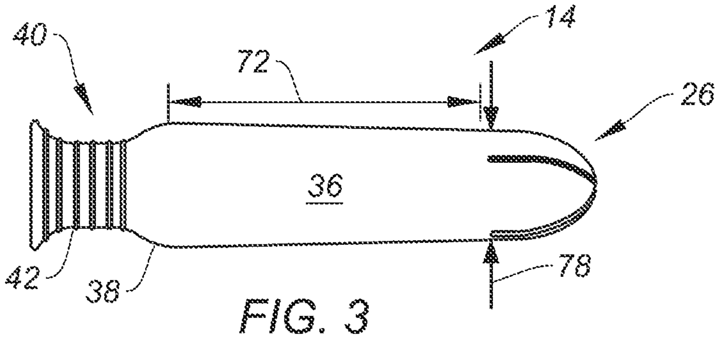
FIG. 3 shows a tampon applicator with a tapered insertion tip.
Figure 4:
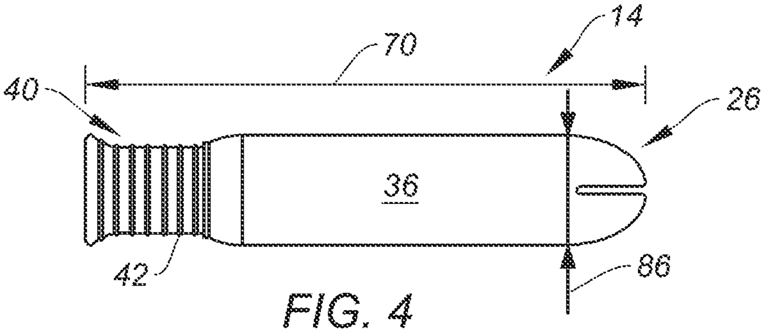
FIG. 4 shows an applicator with a modified insertion tip.
Figure 5:
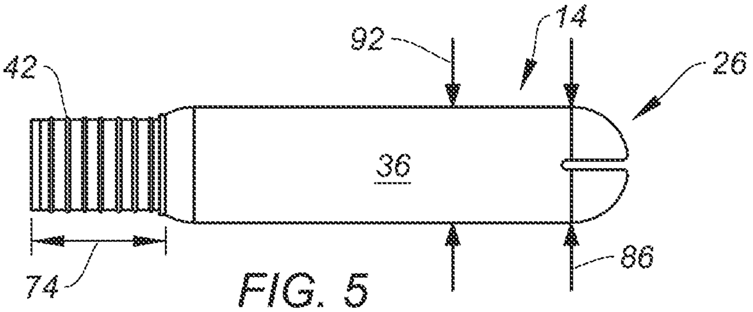
FIG. 5 shows and applicator with a rounded or domed shaped insertion tip.

FIG. 1 shows a tampon applicator that has a largely hemispherical insertion end where the inflection region is substantially the same as the insertion tip (i.e. the length of the inflection curvature corresponds to the length of the formed petals). FIG. 2 shows a tampon applicator 12 with an insertion end 26 that is significantly tapered compared to that of the tampon applicator 12 of FIG. 1. The tampon applicator 12 of FIGS. 2-3 also show a barrel 14 with a main body region 36 that is tapered slightly as one progresses toward the insertion end 26, and is tapered more significantly as one progresses toward the finger grip region 40. The applicator 12 of FIGS. 1, 4-5 demonstrate a more linear main body region 36.

The tampon applicator 12 of the present disclosure may contain a barrel 14 that comprises either a linear or tapered main body region 36, and typically comprises a textured 42 finger grip region 40, although some embodiments may lack a well-defined textured 42 finger grip region 40. The textured 42 finger grip region 40 include ribs, embossing, slits, and/or other three-dimensional topographies.

The tampon applicator 12 of the present disclosure has a tapered insertion end 26 defined in part by a taper ratio. The taper ratio is defined by the boundary of the insertion end 26. That is, where the inflection region 34 extends beyond the insertion tip region 32, the "boundary" is defined by the length, diameter and radius of the inflection curve 54 (i.e. the length 62 of the insertion tip region 32 and any additional length 66 provided by the inflection region 34, and the diameter 86 and radius 82 of the inflection region). Alternatively, where the inflection region 34 overlaps the insertion tip region 32, the "boundary" is defined by the length, diameter and radius of the insertion tip region 32 (i.e., the length 62 of the insertion tip region 32, and the diameter 78 and radius 80 of the insertion tip region 32). As such, the taper ratio of the insertion tip region 32 is defined by the ratio of the length of the taper projection along a longitudinal axis 11 of the barrel 14 (i.e. the formed length 62 of the insertion tip region 32) to the length of the taper projection along a radius 80 of the barrel 14 at the termination 50 of the plurality of slits 48 of the insertion end. The taper ratio of the insertion end 26 having an insertion tip region 32 and an inflection region 34 is defined by the ratio of the length of the taper projection along the longitudinal axis 11 of the barrel 14 (i.e., the formed length 66 of the inflection curve 54, typically including the formed length 62 of the insertion tip region 32 and the addition or subtraction of the formed length 66 of the inflection region 34). For example, FIGS. 7, 8, and 9 shows schematic drawings of the tapered insertion end 26 such as found in a tampon applicator 12 of FIGS. 1-5. For clarity, any number without an "a" or "b" may be demonstrated in FIGS. 7-9 by either or both of "a" and "b". For instance, if referring to radius 82, it can be thought of in terms of (and as shown in FIGS. 7-9) 82*a* for external dimensions and 82*b* for internal dimensions. The main body region 36 of the barrel 14 is shown in part by the portion left of the vertical axis 13 located at the boundary of the insertion end 26 and the main body region 36, designated by diameter 86 (including radii 82), the insertion end 26 is shown by the curved portion (i.e. inflection curve 54) to the right of diameter 86 (as represented by 86*a* for external geometry and 86*b* for internal geometry). As shown throughout the present disclosure, vertical axis 13 is shown along various positions of the length of tampon applicator assembly 10 and is not so limited to a particular location (so long as it is perpendicular to longitudinal axis 11). The length of the taper projection along the longitudinal axis 11 of the barrel 14 is shown by longitudinal axis 11 and designated by lengths 62 and 66, and the projection length along the vertical axis 13 is shown by the line radii 82. A tapered insertion end 26 has a taper ratio, of (a) 62 and any deviation caused by formed inflection region 34 length 66, (b) divided by radius 82, that is greater than 1.

Figure 6A:
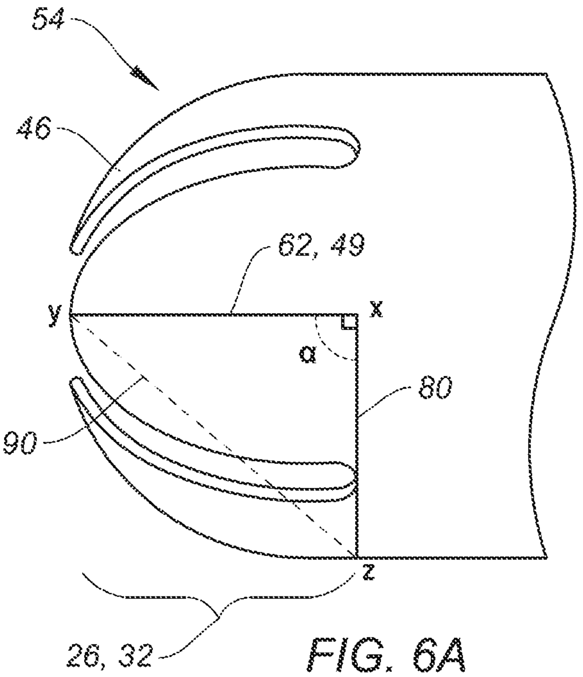

FIG. 6*a*, as discussed below, is a schematic drawing of the same portion of a barrel having an essentially hemispherical, dome shaped insertion end, wherein the length 49 of the petals 45 is roughly equal to the radius 80, resulting in a taper ratio of 1. While a tapered insertion tip (i.e. having a taper ratio of greater than 1) is preferred, various embodiments throughout the present disclosure have benefits with a taper ratio of less than or equal to 1.

The tampon applicator 12 of the present disclosure has a tapered insertion end 26 with a taper ratio of at least 1.0, or 1.2, or typically at least 1.3 and in many cases 1.4, 1.5, 1.6, 1.7 or higher.

In some embodiments, it is advantageous to modify the insertion end 26 such that the insertion end 26 extends beyond the base region 47 of the petals 45 (i.e. beyond the slits 48 between the petals 45). In these embodiments, the insertion end 26 includes a portion extending to the base region 47 of the petals 45 which is an inflection region 34 beyond the insertion tip region 32 and up to the main body region 36. In these embodiments, an inflection curvature 54 extends from the free end 46 of the petals 45 as defined by (or defining) the insertion end 26 and continues to have a portion of the inflection curvature 54 beyond the base region 47 of the petals 45 and up to the main body region 36 in the inflection region 34. This portion between the base region 47 of the petals and the main body region 36 is described as the inflection region 54.

Alternatively, in some embodiments, the inflection region 54 and insertion tip region 32 overlap and/or at least partially coincide. In these embodiments, the inflection curvature ends 54 at an axial length 62 of the petals 45 between the free end 46 of the petals 45 and the base region 47 (i.e. where the slits 48 between the petals 45 terminate 50). In these embodiments, the inflection region 34 is the portion of the length 66 between the end of the inflection curvature 54 and the termination 50 of the slits 48 separating the petals 45.

Figure 6B:
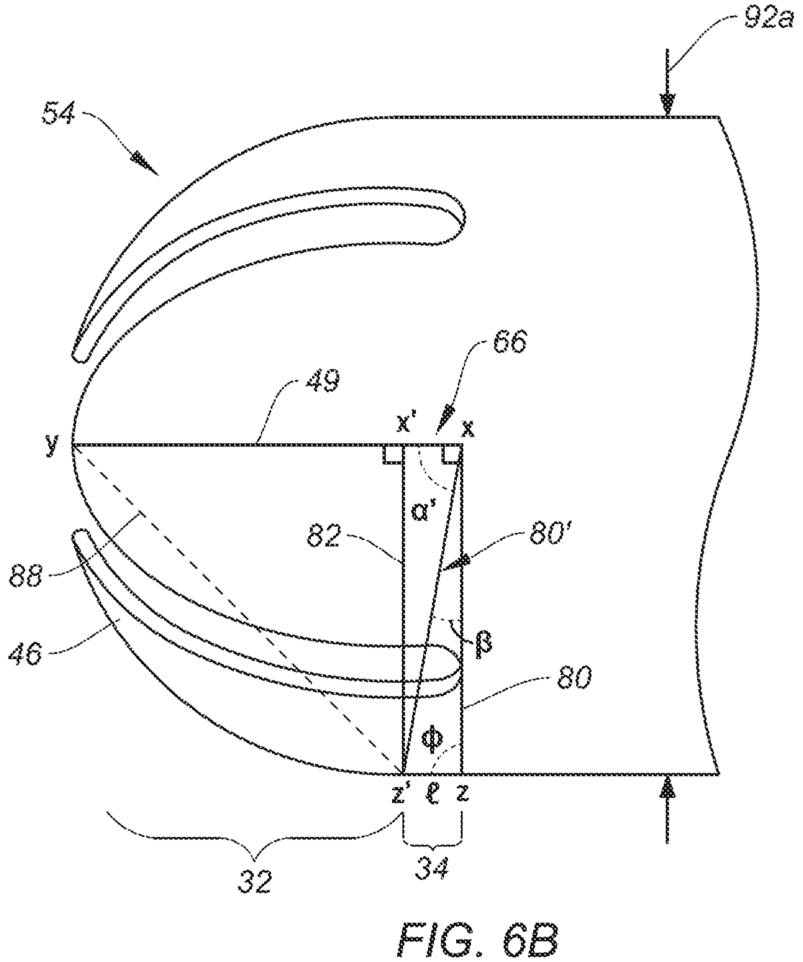
Figure 6C:
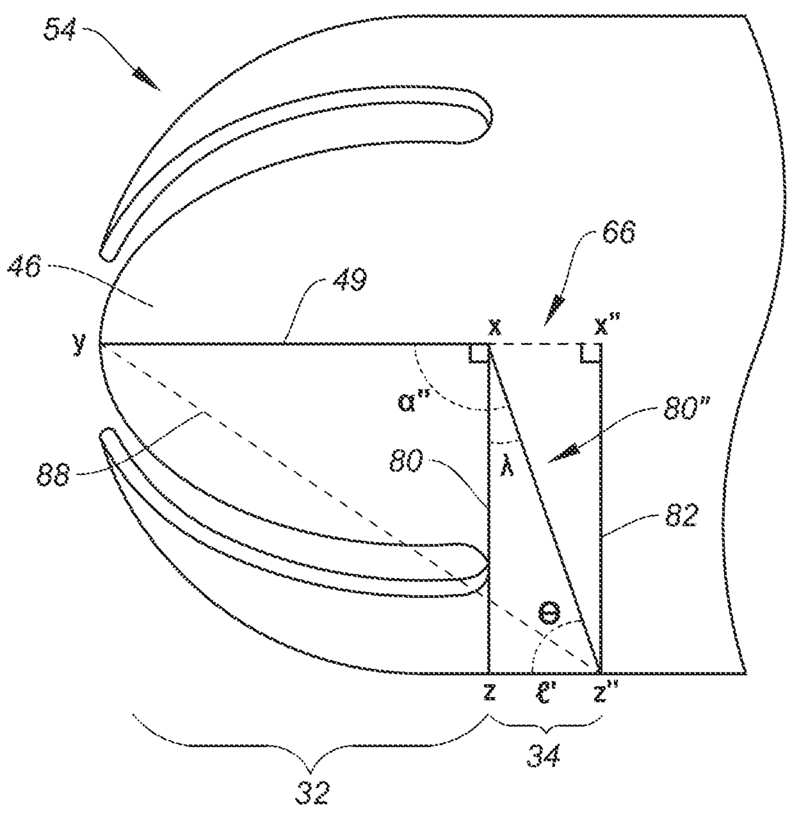

FIGS. 6*a*-6*c* demonstrate configurations of the present disclosure demonstrating variations of the insertion end 26. FIGS. 6*a*-6*c* demonstrate hypotenuses 88 and 90 corresponding to the radii of the insertion end 26. FIG. 6*a* demonstrates an embodiment of the present disclosure where the insertion end 26 corresponds to the insertion tip region 32. The axial length of the petals 49 between points “y” and “z” and insertion tip region radius 80 (between points “z” and “x”) form right angle $\alpha$. Hypotenuse 90 corresponds to points “y” and “z”.

FIG. 6*b* demonstrates an embodiment of the present disclosure where the insertion end 26 is “under-formed”. That is, the insertion tip region 32 and the inflection region 34 overlap. Inflection region 34 axial length 66 is bounded by “x” and “x'”, while the insertion tip region 32 has an axial length 49 between “x” and “y”. Insertion tip region 32 has been otherwise shifted due to the under-formed insertion end-radius 80 has now become 80' due to the shift of point “z” to “z”. Angle $\alpha$ is the sum of angles $\alpha'$ and $\beta$, where $\alpha'$ is formed via the deviation of “z'” and the inflection region 34. Angle $\varphi$ is a complementary exterior angle of angle $\alpha$ to the extent the axial length of the inflection region 66 (or 68) is parallel to length l. Otherwise, angle $\varphi$ is other than a right angle. Hypotenuse 88 of inflection curve 54 is shortened and steeper, albeit FIG. 6*b* only reflects the underlying petal geometry of FIG. 6*a*. In certain embodiments, this reduces ejection force by having petals 45 that extend beyond inflection curve 54. In certain embodiments, this improves petal 45 support and reduces the opportunity for inadvertent petal 45 deflection.

FIG. 6*c* demonstrates an embodiment of the present disclosure where the insertion end 26 is “over-formed”. That is, the inflection region 34 extends the length of the insertion end 26 beyond the insertion tip region 32. Inflection region 34 axial length 66 is bounded by “x” and “x''”, while the insertion tip region 32 has an axial length 49 between “x” and “y”. Inflection region 34 provides the over-formed insertion end 26—radius 80 has now become 80'' due to the shift of point “z” to “z''”. Angle $\alpha$ is extended by angle $\alpha'$; angle $\alpha$ is the sum of angles $\alpha'$ and $\beta$, where $\alpha'$ is formed via the deviation of “z''” and the inflection region 34. Angle $\Theta$ is defined by radius 80'' and length l'. Hypotenuse 88 of inflection curve 54 is longer and more gradual, albeit FIG. 6*c* only reflects the underlying petal geometry of FIG. 6*a*. In certain embodiments, this reduces ejection force, improves insertion comfort, and/or improves petal 45 support and reduces the opportunity for inadvertent petal 45 deflection.

FIGS. 7, 8 and 9 demonstrate configurations of the present disclosure with various aspects and dimensions of both internal barrel 14*a* geometry, external barrel 14*b* geometry, and the thickness 14*c* of the barrel 14. FIG. 7 demonstrate hypotenuses 88 and 90 corresponding to the radii of the insertion end 26. FIGS. 8-9 demonstrate hypotenuses 88 and 90 corresponding to the diameters of the insertion end 26. One skilled in the art understands the hypotenuse for such figures will be different, but that different geometric relationships including a hypotenuse can be drawn in multiple ways, as taught by the present disclosure with respect to diameter and radius, and internal and external dimensions. FIG. 8 demonstrates a barrel 14 prior to formation of the insertion end 26. FIG. 9 shows a barrel 14 with a formed (i.e. domed) insertion end 26, where the insertion end 26 is tapered. FIGS. 8 and 9 are diagrammatic representations and other barrel 14 geometries can be similarly described. The inflection region 34 can be described by both external geometry 14*a* and an internal geometry 14*b*. External geometry relates to, inter alia, how conducive the applicator 12 is to insertion comfort. External geometry 14*a* focuses on a correlation of the external diameter 80*a* of the barrel 14*a* where the slits 48 between the petals 45 terminate 50, and also external diameter 82*a* of the barrel 14*a* at the inflection region 34, and how they compare to the length 62 of the formed petals 45 and length of the inflection region 66 (see, for example, FIG. 9 for an embodiment with formed petals 45). A longer or more gradual taper would be achieved to the extent the length 62 between the free ends 46 of the petals 45 (when formed) and the length 66 of the inflection region 34 (when formed) is greater than the radius of exterior surface 82*a* where the inflection region 34 ends and the main body region 36 begins. In some embodiments, the length between the exterior of the free petal ends 46*a* and the termination 50 of the slits 48 between the petals 45 is greater than the exterior radius 82*a* of exterior surface where the insertion tip region 32 meets the main body region 36. In some embodiments, the length between the exterior of the free petal ends 46*a* and where the inflection region 34 meets the main body region 36 is greater than the exterior radius 82_a_ where the inflection region 34 meets the main body region 36. Similar relationships can be had with internal dimensions, albeit the numbers may vary depending on the thickness 14_c_ of the barrel 14 in the insertion end 26. For instance, internal diameters 80_b_ and 82_b_ correspond to external diameters 80_a_ and 82_a_, respectively, and their respective differences are due to thickness 14_c_. One skilled in the art understands thickness 14_c_ varies in many embodiments.

In some embodiments, in view of the additional length 66 of the insertion end 26 due to the inflection region 34 increasing the inflection curvature 54 beyond the base region 47 of the petals 45, where the axial length 66 of the inflection region 34 does not exceed the diameter 86 where the inflection curvature 54 terminates, a correlation can be drawn between (a) the axial length 62 of the insertion tip region 32, (b) the axial length 66 of the inflection region 34, and (c) the hypotenuse 88 of the inflection curve 54 can also be thought of by the following equation:

$$\text{hypotenuse 88 of the inflection curve 54} > \sqrt{(\text{axial length of the insertion tip region})^2 + (\text{axial length 62 of the insertion tip region 32} + \text{axial length 66 of the inflection region 34})^2}$$

For clarity, above equation is not a usage of the Pythagorean theorem, as it does not reflect three sides of a right triangle. Rather, it demonstrates that in certain embodiments, the square of the hypotenuse 88 of the inflection curve 54 is greater than the sum of the squares of the aforementioned axial lengths 62, 66. In other words, the insertion end 26 is lengthened 62 via the inflection region 34 by a distance less than the diameter 86 of the barrel 14 where the inflection curve 54 terminates and thus what normally might be hypotenuse 90 for the insertion tip region 32 (i.e. the hypotenuse 90 from the free petal ends 46 to the termination 50 of the slits 48 between the petals 45). This concept can be utilized in both formed and unformed states, as it relates to external geometry and also to internal geometry 14_b_ as discussed below. For instance, diameter 86 is referred to as diameter 86_a_ in the context of external geometry and diameter 86_b_ in the context of internal geometry 14_b_, and likewise, hypotenuse 88 and 90 are 88_a_ and 88_b_ and 90_a_ and 90_b_ for external "a" and internal geometries "b". Also likewise, the insertion tip region 32 lengths 62 and 64, in the formed and unformed states, respectively, would be 62_a_ and 64_a_, respectively, as it relates to external geometry 14_a_, and 62_b_ and 64_b_, respectively, as it relates to internal geometry 14_b_. Additionally, the inflection region 34 lengths 66 and 68, in the formed and unformed states, respectively, would be 66_a_ and 68_a_ in the formed and unformed states, respectively, as it relates to external geometry 14_a_, and would be 66_b_ and 68_b_ in the formed and unformed states, respectively, as it relates to internal geometry 14_b_. Further, while the inflection curvature 54 is determined when in the formed state, inflection curvature 54 also has an unformed length 68 that can be determined by geometric calculations of the insertion end 26 in the formed state. Likewise, the insertion tip region 32 has an unformed length 64.

Internal geometry 14_b_ relates to, inter alia, ejection efficiency. Internal geometry 14_b_ focuses on a correlation of the internal diameter 80_a_ of the barrel 14 where the slits 48 between the petals 45 terminate 50, and internal diameter 82_a_ describes the internal diameter at the inflection region 34; internal geometry correlates how either or internal diameters 80_b_ and 82_b_ compare to the length 62 of the formed petal 45. A longer or more gradual taper that is more conducive towards ejection efficiency would be achieved to the extent the length 62 between the free ends 46 of the petals 45 (when formed) length 66 of the inflection region 34 (when formed) is greater than the radius of interior surface 82_b_ surface 82_a_ where the inflection region 34 ends and the main body region 36 begins. In some embodiments, the length between the interior surface of the free ends 46_b_ of the termination 50 of slits 48 of the petals 45 is greater than the interior radius 80_b_ of the barrel 14 where the insertion tip region 32 meets the main body region 36. In some embodiments, the length between the interior of the free petal ends 46_b_ and where the inflection region 34 meets the main body region 36 is greater than the interior radius 82_b_ where the inflection region 34 meets the main body region 36.

The internal hypotenuse 88_b_ and/or 90_b_ is particularly useful in that also describes how well the pledget 22 nests within the insertion end region 26, which contributes to improved insertion ease. A pledget 22 shaped such that at least a portion of the pledget 22 intersects the internal hypotenuse 88_b_ and/or 90_b_ indicates the pledget 22 supports at least a portion of the insertion tip end 26. In some embodiments, the pledget 22 intersects the insertion tip region 26 hypotenuse 88 and/or 90. In some embodiments, the pledget 26 intersects the inflection curve hypotenuse 90. In yet other embodiments, the pledget 22 intersects both the insertion tip region 26 hypotenuse 88 and the inflection curve 54 hypotenuse 90. While the internal geometry 14_b_ is preferred, for simplicity, measurements can be made from external geometries 14_b_ as well where the thickness 14_c_ is small. Said differently, applicators 12 are typically thin parts and as such, the pledget will likely intersect any such internal hypotenuse 88_b_ or 90_b_ if pledget 22 intersects external hypotenuse 88_a_ or 90_a_. Further, the hypotenuse 88 and/or 90 is to be calculated in the formed state. In some embodiments, the pledget 22 supports at least the free ends 46 of the petals 45 as the pledget 22 is ejected. While some embodiments have a pledget 22 shape that is substantially similar to the insertion end region 26, some embodiments do not require such as insertion into the body necessitates bodily forces that press upon the applicator 12 (i.e. at the insertion end region 26) and thus push the insertion end 26 into contact with the pledget 22. As such, to the extent the insertion end region 26 and pledget 22 shape are somewhat similar in at least some of the characteristics described throughout the present disclosure, greater insertion ease or comfort is achieved and improved.

External geometry 14_a_, as it relates to internal geometry 14_b_ also impacts ejection efficiency. A thinner petal 45 typically deflects under less force than a thicker petal 45, and as such, the relative thickness 14_c_ of the petal 45 can impact ejection efficiency. As it may be difficult to create a very thin petal 45, portions of the petal 45 may be locally thinner than other portions of the petal 45, and provide improved ejection efficiency. These locally thinner regions can provide an aesthetic that indicates to the consumer that the applicator 12 has improved insertion ease (i.e. at least one of ejection efficiency and insertion comfort).

The present disclosure further contemplates elongated petals 45. It has also been found that increasing the length 49 of the petals 45 will also decrease the amount of force required to eject a pledget 22 from the barrel 14 thus improving ejection efficiency. Note that petal length 49 in various embodiments, is the same as either or both of the length 62 (or 64) insertion tip region 32 and the length 66 (or 68) of the inflection region 34. Similarly, and as taught throughout the present disclosure, petal length 49_a_ regards external geometry 14_a_ and petal length 49_b_ corresponds to internal geometry 14*b*. For example, consider a slit 48 in FIG. 18. As shown in FIG. 17, extending the slit 48 further into the main body region 36 of the barrel 14 will decrease the ejection force required to operate the tampon applicator 12.

Extending the slit 48 as suggested also changes the shape of the petal 45 and the taper ratio. That is, a petal 45 that was largely a semi-circle or parabola now has a portion near the base region 47 that is largely linear. For example, FIGS. 17 and 18, each show a flat section of a petal 45 design, the petal 45 of FIG. 18 being almost entirely curved and having no linear section or only a small linear section, and FIG. 17 shows a petal 45 with a curved region similar to that of FIG. 18, but the petal 45 of FIG. 17 has a longer linear section as shown as the region between the two dashed lines 98 and 100. It can be appreciated that increasing the length 49 of the petal 45 will increase the taper ratio of the insertion tip, even if this is accomplished by extension of a linear region.

The present disclosure further contemplates insertion end 26 configurations having varying spacing amongst the petals 45. FIGS. 10-11 represents the front view of an insertion end 26 having four petals 45 wherein the petals 45 are separated by a slit 48 which runs parallel to the longitudinal axis 11 of the tampon applicator 12. The slits 48 at the free end 46 of the petals 45 region makes an "X" shape. At the forward most end 44 (i.e. at the free end of the petals 45), there is also an opening 30, much smaller than the diameter 92 of the main body region 36 of the barrel 14. As discussed throughout the present disclosure, diameter 92*a* is the external diameter (of the main body region 36), while diameter 92*b* is the internal diameter (of the main body region 36) The opening 30 further separates the free ends 46 of the petals 45. The opening 30 is shown by the center portion of the "X" or the intersection of the two slanted lines of the "X". FIG. 12 is a schematic drawing of the front view of the applicator insertion end 26 of FIG. 10 wherein the dotted line represents an inscribed circle 58 of the opening 30 as defined above and the larger outer circle represents the interior diameter 92*b* of the barrel 14 where the barrel 14 meets the insertion end 26. The degree of closure is defined as the ratio of the diameter 60 of the insertion end 26 opening 30 to the interior diameter 92*b* of the barrel 14 where the insertion end 26 adjoins the main body region 36 of the barrel 14.

The closure diameter (i.e. the insertion end opening 30) and its impact on ejection force is demonstrated in the below Table 1:

TABLE 1

Closure Diameter vs. Ejection Force

| Metric | Range | | Δ |
|---|---|---|---|
| Closure Diameter | 0.075 in | 0.150 in | 0.075 in |
| Ejection Force | 6 N | 3.5 N | 2.5 N |

The above Table 1 demonstrates the ability to modify ejection force by one (1) Newton (3.6 ounces) by changing the closure diameter 30 by 0.76 mm (0.030 inches). In other words, one can increase or decrease ejection force by one (1) Newton by increasing or decreasing, respectively, the closure diameter 30 by 0.76 mm. Another way to describe the relationship of closure diameter 30 and ejection force is by modifying the closure diameter 30 by 1 mm (0.039 inches), the ejection force is modified by 1.312 Newton (4.719 ounces).

It has been found, as demonstrated above, that enlarging the insertion end 26 opening 30 will decrease the amount of force required to eject a pledget 22 from the barrel 14. This effect is relatively more pronounced in an insertion end 26 with a larger taper, e.g., the insertion end 26 shown the schematic of FIG. 7, than in a blunter or more spherical insertion end 26, e.g., the insertion end 26 shown the schematic of FIG. 6.

The length 49 of the petals 45 also influence ejection force, as demonstrated in the below Table 2:

CHART 2

Petal Length vs. Ejection Force

| Metric | Range | | Δ |
|---|---|---|---|
| Petal Length | 8.5 mm | 12.5 mm | 4 mm |
| Ejection Force | 5.5 N | 2.5 N | 3 N |

The above Table 1 demonstrates the ability to modify ejection force by one (1) Newton (3.6 ounces) by changing the petal 45 length 49 by 1.33 mm (0.052 inches). In other words, one can increase or decrease ejection force by one (1) Newton by increasing or decreasing, respectively, the petal 45 length 49 by 1.33 mm. Another way to describe the relationship of petal 45 length 49 and ejection force is by modifying the petal 45 length 49 by 1 mm (0.039 inches), the ejection force is modified by 0.75 Newton (2.698 ounces).

Petal 45 gap 51 geometry describes the petal slit 48 at the base region 47 of the petals 45 and is also within the scope of the present disclosure. A tear-drop shaped gap 51 improves insertion ease. The radius of curvature 52 of the gap 51 is between about 0.028 inches and about 0.030 inches. The diameter of the gap 51 is between about 0.020 inches and about 0.056 inches. In some embodiments, a gap 51 between adjacent petals 45 is greater than about 0.005 inches.

The insertion end 26 has a radius of curvature 96 between about 0.200 inches and about 0.420 inches. In other embodiments, the insertion end 26 has a radius of curvature 96 exceeding about 0.400 inches, or exceeding about 0.420 inches. In some embodiments, the insertion end 26 has a first radius of curvature 96*a* between about 0.202 inches and about 0.220 inches. In some embodiments, the insertion end 26 has a second radius of curvature 96*b* between about 0.336 inches and about 0.409 inches. In some embodiments, the insertion end 26 has a third radius of curvature 96*c* between about 0.373 inches and about 0.392 inches. In some embodiments, the insertion end 26 has a radius of curvature 96 between about 0.201 inches and about 0.399 inches.

The insertion end 26 of the present disclosure is at least ten percent (10%) of the length 70 of the entire formed applicator barrel 14. In some embodiments, the length 70 is between about 2.0 and about 3.5 inches, and more preferably between about 2.5 and 3.0 inches. In some embodiments, the length is greater than about 2.0 inches, or less than about 3.5 inches. In further embodiments, the length is between about 2.75 inches and 3.0 inches. In some embodiments, the length of the insertion end 26 is at least fifteen percent (15%) of the length 70 of the entire formed applicator barrel 14. In further embodiments, the length of the insertion end 26 is at least twenty percent (20%) of the length 70 of the entire formed applicator barrel 14. Recall the insertion end 26 length is either or both of the length 62 or 64, respectively, of the insertion tip region 32 and/or the length 66 or 68, respectively, of the inflection region 34, depending on the embodiments as discussed throughout the present disclosure.

The length 72 of the main body region is at least 1.25 inches, or up to about 2.0 inches, and more preferably between 1.25 inches and 1.75 inches. The length 74 finger grip region 40 is at least about 0.5 inches, or up to about 1.0 inches, and more preferably between about 0.50 inches and about 0.75 inches. The length 76 of the reverse taper region 38 is at least 0.10 inches, or up to about 0.5 inches, or more preferably between about 0.125 inches and about 0.4 inches.

Applicators 12 of the present disclosure can be modeled similarly to a modified cantilevered beam equation. Such a model, referred to as the applicator deflection modulus, relates the number of petals 22, Young's Modulus, the moment of inertia, deflection, petal 45 length 49, the width 43 of the petal 45, thickness 14*c* of the petal 45 at its base region 47, the diameter 78 of the barrel 14 at the termination 50 of the slits, and the radius of curvature 52 of the gap 51 between adjacent petals 45 at their base regions 47. The model has been verified against currently known applicators, including the PLAYTEX SPORT applicator and PLAYTEX GENTLE GLIDE APPLICATOR. Inventive samples of the present disclosure have also been modeled. The model provides a basis for modifying certain aspects of the insertion end 26, insertion tip region 32, inflection region 34, and/or petals 45 to promote improved tampon assembly 10 performance.

The aforementioned cantilever beam equation is defined as follows, from both a petal length standpoint and a petal thickness standpoint:

Cantilever Beam Equation—Petal Thickness

Definitions $F_{pb}$=Petal Bending Force
$F_e$=Ejection Force
N=Number of Petals
E=Young's Elastic Modulus
I=Second Moment of Inertia
$L_f$=Formed Petal Length
δ=Deflection
b=Width of the Petal at the Base
t=Thickness of the Petal
$d_{barrel}$=Outer Diameter of the Barrel at the Petal Base
$d_{tear}$=Diameter of the "Tear Drop" in the Petal Bending Force for a Single Petal:

$$F_{pb} \approx \frac{3EI}{L_{f^3}}\delta$$

Ejection Force for Multiple Petals:

$$F_e \approx NF_{pb} \approx N\frac{3EI}{L_{f^3}}\delta$$

$$I = \frac{bt^3}{12}$$

$$b = \frac{\pi d_{barrel} - Nd_{tear}}{N} F_e \approx \frac{3NE\left(\frac{bt^3}{12}\right)}{L_{f^3}}\delta \approx \frac{3NEbt^3}{12L_f^3}\delta \approx \frac{3NE\left(\frac{\pi d_{barrel} - Nd_{tear}}{N}\right)t^3}{12L_f^3}\delta$$

$$F_e \approx \frac{3NE(\pi d_{barrel} - Nd_{tear})t^3}{12NL_f^3}\delta$$

-continued $$F_e \approx \frac{3E(\pi d_{barrel} - Nd_{tear})t^3}{12L_f^3}\delta$$

Converting Ejection Force to Ounces:

$$F_e \approx 16\frac{3E(\pi d_{barrel} - Nd_{tear})t^3}{12L_f^3}\delta$$

Assuming E has units of psi, and $d_{barrel}$, $d_{tear}$, t, $L_f$, and δ have units of inches.

Cantilever Beam Equation—Petal Thickness

Definitions $F_e$=Ejection Force
N=Number of Petals
E=Young's Elastic Modulus
I=Second Moment of Inertia
$L_f$=Formed Petal Length
δ=Deflection
b=Width of the Petal at the Base
t=Thickness of the Petal
$d_{barrel}$=Outer Diameter of the Barrel at the Petal Base
$d_{tear}$=Diameter of the "Tear Drop" in the Petal
$t_e$=effective thickness
$t_{max}$=Maximum Petal Thickness
$t_{min}$=Minimum Petal Thickness
α=Percentage of "Thick" Petal Regions ($0<\alpha<1$)
β=Percentage of "Thin" Petal Regions ($0<\beta<1$)
n=Number of Regions of Thickness "i"
$t_i$=Thickness "i"
$\epsilon_i$=Percentage of $t_i$ throughout the Petal Ejection Force for Multiple Petals:

$$F_e \approx \frac{3E(\pi d_{barrel} - Nd_{tear})t^3}{12L_f^3}\delta$$

Effective Thickness Expressed as a Function of Two Different Thicknesses:

$$t_e = \alpha t_{max} + \beta t_{min}$$

Effective Thickness Expressed as a Function of as a Series of Thicknesses:

$$t_e = \sum_{i=1}^{n} \epsilon_i t_i$$

Ejection Force Based for a Petal with Varying Thicknesses;

$$F_e \approx \frac{3E(\pi d_{barrel} - Nd_{tear})t_e^3}{12L_f^3}\delta$$

$$F_e \approx \frac{3E(\pi d_{barrel} - Nd_{tear})(\alpha t_{max} + \beta t_{min})^3}{12L_{f^3}}\delta; \text{ or}$$

-continued $$F_e \approx \frac{3E(\pi d_{barrel} - N d_{tear})\left(\sum_{i=1}^{n} \epsilon_i t_i\right)^3}{12L_f^3}\delta$$

Ejection Force for a Petal with Varying Thicknesses in Ounces:

$$F_e \approx 16\frac{3E(\pi d_{barrel} - N d_{tear})\left(\sum_{i=1}^{n} \epsilon_i t_i\right)^3}{12L_f^3}\delta$$

Assuming E has units of psi, and $d_{barrel}$, $d_{tear}$, t, $L_f$, and $\delta$ have units of inches.

Many tampon applicators 12 are made from plastic materials, and as such, the Modulus of Rigidity is generally between about 27,000 psi and about 70,000 psi.

FIGS. 19-20 shows and angled view of the barrel 14, highlighting a petal 45 width 43 in the formed state, as well as a petal 45 gap 51 and slit 48. Petal 45 width 43 (and slit 48 or gap 51) can vary along the length 49 of the petal 45, but is generally found by taking the circumference of the applicator about a portion of the barrel 14 in the petal 45 base region 47 and subtracting out the diameter of the slits 48 or gaps 51, and then dividing by the number of petals. The petal 45 widths 43 of the present disclosure vary from between about 0.14 inches to about 0.68 inches. In some embodiments, petal 45 widths 43 are between about 0.20 inches and about 0.45 inches, and in yet other embodiments, are between about 0.24 inches and about 0.42 inches. In yet further embodiments, petal 45 widths 43 are between about 0.25 inches and about 0.40 inches.

Chart 3 below describes some embodiments using theoretical and actual measurements:

GLIDE theoretical numbers deviate from actual. Nonetheless, as demonstrated by the above Chart 3, the theoretical model does demonstrate how the petal gap 51 and petal length 49 can impact ejection force. Chart 3 is exemplary and not limiting.

It can also be appreciated that other changes to the shape of the curved portion of the petal 22, e.g., a blunter terminus, difference in the slope along portions of the curve or along the entire curve, can also affect ejection force or insertion comfort. Further, the degree of curl inwards toward the longitudinal axis 11 of the barrel 14 can have an impact on these features.

The tampon applicator 12 of the present disclosure also has specific performance features, for example, from about 5 oz. to about 25 oz. of ejection force is required to eject a pledget 22 from the barrel 14 of the tampon applicator 12, typically less than 25 oz., e.g., 20 oz or less is required, and often 15 oz. or less is required to eject a pledget 22. Thus, in various embodiments, the tampon applicator 12 requires from about 8 to about 20 oz., i.e., 2.2 to 5.6 N, e.g., about 10 to about 20 oz, i.e., 2.8 to 5.8 N, about 10 to about 15 oz., i.e., 2.8 to 4.2 N, or about 10 to about 12 oz., i.e., 2.8 to 3.3 N, to eject the pledget 22.

Embodiments of the present disclosure provide tampon applicators 12 incorporating one or more of these findings. A general embodiment of the present disclosure provides a tampon applicator 12 comprising a plunger 16 and a barrel 14, said barrel 14 being generally tubular in shape and comprising a main body region 36 having a generally circular or elliptical hollow interior cavity 15, a forward most end 44 that defines a tapered insertion end 26 formed by from 3 to 8 petals 45, the insertion end 26 terminates at an opening 30 defined by the free ends 46 of petals 45. The insertion end 26 has a generally circular or elliptical shape that is similar to that of the hollow interior cavity 15 of the main body region 36 where the insertion end 26 adjoins the main body region 36, and a rearward most end 84 opposing

CHART 3

Theoretical and Actual Ejection Forces

| Sample | Formed Petal Length (mm) | Formed Petal Length (in) | R1 (in) | Gap Radius (in) | Slit Length (in) | Total Slit Length (in) | R1/Total Slit Length | Sample Slit Length-Gentle Glide Slit Length (in) | Theoretical Ejection Force (oz) | Actual Ejection Force (oz) | Actual Ejection Force (N) |
|---|---|---|---|---|---|---|---|---|---|---|---|
| Current GENTLE GLIDE | | | 0.576 | 0.028 | 0.403 | 0.431 | 1.336 | 0.000 | 18.866 | 13.800 | |
| Current SPORT | | | 0.955 | 0.010 | 0.592 | 0.602 | 1.586 | 0.171 | 8.451 | 9.840 | |
| Sample 0 | | | 0.955 | 0.010 | 0.530 | 0.540 | 1.769 | 0.109 | 11.839 | 10.500 | |
| Control | 8.743 | 0.344 | 0.576 | 0.028 | N/A | 0.431 | 1.336 | N/A | N/A | 18.895 | 5.253 |
| Sample A | 10.293 | 0.405 | 0.576 | 0.028 | | 0.501 | 1.150 | | | 13.862 | 3.854 |
| Sample B | 10.704 | 0.421 | 0.576 | 0.028 | | 0.521 | 1.106 | | | 13.507 | 3.755 |
| Sample C | 11.220 | 0.442 | 0.576 | 0.028 | | 0.541 | 1.065 | | | 11.663 | 3.243 |
| Sample D | 11.991 | 0.472 | 0.576 | 0.028 | | 0.561 | 1.027 | | | 10.260 | 2.852 |
| Sample E | 12.394 | 0.488 | 0.576 | 0.028 | | 0.581 | 0.991 | | | 9.800 | 2.724 |
| Sample F | | | 0.576 | 0.028 | 0.592 | 0.620 | 0.929 | 0.189 | 7.532 | N/A | N/A |
| Sample G | | | 0.576 | 0.028 | 0.530 | 0.558 | 1.032 | 0.127 | 10.816 | | |
| Current Radient | | | 0.360 | 0.018 | 0.328 | 0.346 | 1.040 | N/A | 25.173 | 17.190 | |

The model is based on a known hemispherical insertion tip such as that of the PLAYTEX GENTLE GLIDE. Due to this basis in the theoretical model, the PLAYTEX GENTLE the forward most end 44, said rearward most end 84 having an opening 31 in which the plunger 16 is slideably disposed, wherein the insertion end 26 has a taper ratio as defined above of from about 1.3 to about 3.5, and the insertion end 26 opening 30 has a degree of closure as defined above of from about 0.1 to about 0.3, which tampon applicator 12 requires an ejection forces of from about 5 to about 25 oz to eject an absorbent pledget 22.

In most embodiments the barrel 14 has a circular interior, i.e., a cross section of the main body region 36 of the barrel 14 defines an enclosed circle, and the insertion end 26 opening 30 has an inscribed circle 60. It should be understood that the actual shape of the insertion end 26 opening 30 is not that of a simple circle—the shape of the free ends 46 of the petals and the size of the slits 48 defining the petals 45 create an irregular shaped opening 30. Circular as used in relationship to the insertion end 26 opening 30 means that a regular curved figure described by the free ends 46 of the petals 45 is in this case circular as opposed to elliptical.

In many embodiments the insertion end 26 is formed by from 3 to 6 or 3 to 5 petals 45, e.g., 3, 4 or 5 petals 45.

The ejection force of a tampon applicator 12 of the present disclosure is no greater than 25 oz. In many embodiments the required ejection force is from about 8 to about 20 oz. In many preferred embodiments the required ejection force is from about 10 to about 20 oz, or from about 10 to about 15 oz, for example, from about 10 to about 12 oz.

In many embodiments the tampon applicator 12 has a taper ratio of from about 13 to about 2.5, for example a taper ratio of at least 1.5, 1.6 or 1.7, up to about 2.3, 2.2 or 2.0, and in many embodiments the tampon applicator 12 has a degree of closure of from about 0.1 to about 0.25, from about 0.1 to about 0.20, e.g., from about 0.12 to about 2.0 or about 0.14 to about 0.25.

The taper of the tampon applicator 12 is related to the outside dimensions 14*a* of the applicator 12, while the degree of closure is related to the interior dimensions 14*b*. The direct relationship between taper and degree of closure is through the thickness 14*c* of the barrel 14 wall where the main body region 36 adjoins the insertion end 26 and the thickness 14*c* of the petals 45 at their free ends 46. The thickness 14*c* of the barrel 14 wall and the petals 45 of the present disclosure are typical of those encountered in the art, and will vary somewhat.

As discussed above, in light of reduction in ejection force due to the present the reconfiguration of the insertion end 26, it may be possible to prepare applicators 12 with somewhat thicker petals 45, which may prevent unwanted deformation of the insertion end 26. For example, while in many embodiments the petals 45 will have a thickness in the ranges found in U.S. Pat. No. 8,444,590, e.g., about 0.004 inches to about 0.022 inches, about 0.008 inches to about 0.018 inches, or about 0.009 inches to about 0.013 inches, many embodiments the thickness of the petals 45 may be at the higher end of such ranges. In some embodiments the petals 45 can be thicker than those of U.S. Pat. No. 8,444,590, for example, up to 0.025, 0.03 or 0.035 inches.

Generally, the petals 45 have a high degree of thickness uniformity. Petal 45 thickness 14*c* uniformity across the entire area of each petal 45 is advantageous for several reasons. First, it can result in processing efficiencies when making the applicator 12. Secondly, a uniform thickness 14*c* ensures that each petal 45 will function properly both during storage and shipment of the applicator 12, and more importantly during use by a woman. In addition, the uniform petals 45 may be more aesthetically pleasing to the consumer.

In many embodiments of the present disclosure, the thickness 14*c* measured at any point on a given petal 45 does not vary more than about 25% across the entire area of the petal 45, often the thickness 14*c* does not vary more than about 10% across the entire area of the petal 45 and in some embodiments the thickness 14*c* does not vary more than about 2% across the entire area of the petal 45.

The barrel 14 and the plunger 16 may be prepared from the same material or from different materials, and likewise for embodiments with a two-piece plunger 16 having an inner plunger 18 and an outer plunger 20, the materials. For example, the tampon applicator 12 plunger 16 and/or barrel 14 may be prepared from cardboard, but in many embodiments, at least a portion of the tampon applicator 12, e.g., the barrel, or the entire applicator is prepared from a composition comprising a thermoplastic polymer, an elastomeric polymer, or a mixture of a thermoplastic and elastomeric polymer. For example, the tampon applicator may be made from a polymer composition comprising one or more synthetic polymers and/or naturally occurring materials such as a polyolefin polymer or copolymer, polyester, polyamide, polystyrene, polyvinyl chloride, polyacrylate, polymethacrylate, polyvinyl alcohol, polylactic acid or moldable starch. Most often the polymer will comprise a thermoplastic polymer or a blend of a thermoplastic and elastomeric polymer, for example, the polymer often comprises a polyethylene, low density polyethylene, high density polyethylene, near low density polyethylene, polypropylene, or a copolymer comprised of ethylene, styrene, isoprene or butadiene monomers. In many embodiments the organic polymer comprises low density polyethylene, high density polyethylene or a mixture of low density polyethylene and high density polyethylene.

In some embodiments, the organic polymer comprises a blend of a polyethylene, e.g., low-density polyethylene and a thermoplastic elastomer. For example, the organic polymer may comprise a blend of about 50 wt. % to about 90 wt. %, e.g., about 80 wt. %, low-density polyethylene and about 50 wt. % to about 10 wt. %, e.g., about 20 wt. %, thermoplastic elastomer, based on a total weight of the composition. On useful thermoplastic elastomer is a tri-block (terpolymer), having an A-B-A configuration of monomers, in which monomer B is not the same as monomer A. Typically the blocks comprise styrene, butadiene, or isoprene monomers. Other classes of useful thermoplastic elastomers include, for example, thermoplastic polyurethane elastomers.

When the tampon applicator 12 comprises a thermoplastic or elastomeric polymer composition, the composition will also typically comprise one or more of a variety of common additives, such as processing aids, stabilizers, lubricants colorants etc. For example, the polymer composition may comprise one or more plasticizers, compatibilizers, flow modifiers, antioxidants, antistatic agents, fillers, reinforcements, surfactants, thermal stabilizers, impact modifiers, processing aids such as stearate salts, lubricants, flame retardants, biocides, antiozonants, blowing agents, antifoaming agents and the like. In order to possess or maintain the proper softness and/or lubricity the composition typically contains at least 0.05 of a lubricant, for example, a lubricant comprising a fatty acid amide such as erucamide, oleamide, stearamide, stearyl erucamide, bis-erucamide, ethylene bis stearamide, ethylene bis oleamide.

Some embodiments of the present disclosure provide a tampon assembly 10 comprising a tampon applicator 12 of the present disclosure and an absorbent tampon pledget 22 contained within the barrel 14 (prior to ejection from the barrel 14 as used inside the body of a user). The pledget 22 may have a shape that corresponds with the interior geometry 14*b* of the main body region 36 of the barrel 12, or at least a portion of the pledget 22 may be shaped to correspond with at least a portion of the interior geometry 14*b* of the insertion end 26 as in U.S. Pat. No. 9,192,522. Suitable materials for forming a pledget 22 include, for example, cellulosic; rayon; cotton; pulp; superabsorbent, such as Oasis; absorbent foam, such as hydrophilic polyurethane foam; or any combinations thereof.

The reconfigured insertion end 26 of the present disclosure furthers the attempts to find a proper balance of both ejection force and petal 45 stability, particularly stability in the free petal ends 46. There is no particular limitation placed on the main body region 36 of the barrel 14 or the plunger 16, each of which may encompass any of the variety of features known in the art.

In this document, the terms "a" or "an" are used, as is common in patent documents, to include one or more than one. In this document, the term "or" is used to refer to a nonexclusive or, unless otherwise indicated. It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the present disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc., as they may be included, are used merely as labels, and are not intended to impose numerical requirements on their objects. In the Detailed Description provided above, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A tampon applicator, comprising:

a barrel having a straight central longitudinal axis, comprising:

an insertion tip region having between three and eight petals, each of the petals having a free end coinciding with a forward most end of an inflection curvature, each of the petals separated from each other by one of a plurality of slits, the insertion tip region having a formed insertion tip region length defined from the free end of the petals to where the slits between the petals terminate, the insertion tip region defining an insertion tip region radius where the plurality of slits between the petals terminate;

an inflection region adjacent to the insertion tip region, the inflection region defining a formed inflection region length, the inflection region having an inflection region radius;

a main body region adjacent the inflection region, the main body region having a main body region radius, the main body region having a wall that is substantially straight; and a grip region adjacent the main body region; and a plunger that telescopically engages the barrel;

wherein each of the petals has a formed petal length of between about 0.40 inches and about 0.48 inches, wherein a total slit length between each of the petals is between about 0.50 inches and about 0.58 inches;

wherein the inflection region radius is located where the inflection region meets the main body region and the inflection region radius is less than the main body region radius;

wherein the petals have a wall thickness that is substantially uniform;

wherein the formed insertion tip region length is different than and separate from the formed inflection region length;

wherein an insertion taper ratio is the ratio between the formed insertion tip region length to the insertion tip region radius, where the insertion taper ratio is greater than 1;

wherein an inflection taper ratio is the ratio between (a) a sum of the formed insertion tip region length and the formed inflection region length, to (b) the greater of the insertion tip region radius and the inflection region radius, where the inflection taper ratio is greater than 1;

wherein the insertion tip region, the inflection region, the main body region and the grip region are coaxial about the straight central longitudinal axis.

2. The tampon applicator according to claim 1, wherein the inflection region is adjacent to and separate from the insertion tip region such that the sum of the insertion tip region length and the inflection region length is greater than the insertion tip region length.

3. The tampon applicator according to claim 1, wherein the inflection region length is less than the inflection region radius.

4. The tampon applicator according to claim 1, wherein the sum of the insertion tip region length and the inflection region length is at least about 10% of a barrel length of the barrel.

5. The tampon applicator according to claim 4, wherein the sum of the insertion tip region length and the inflection region length is at least about 20% of a barrel length of the barrel.

6. The tampon applicator according to claim 1, wherein the inflection region length increases an inflection region curvature beyond where the slits between the petals terminate.

7. The tampon applicator according to claim 1, wherein an angle $\alpha''$ is defined by the insertion tip region length along and the central longitudinal axis to a point x where the slits between the petals terminate, and from the point x where the slits between the petals terminate to where the inflection region meets the main body region at a point z", wherein angle $\alpha''$ is obtuse.

8. The tampon applicator according to claim 1, wherein the inflection taper ratio is greater than 1.3.

9. The tampon applicator according to claim 1, wherein the petal wall thickness does not vary by more than about 10% across an area of each of the petals.

10. The tampon applicator according to claim 9, wherein the petal wall thickness does not vary by more than about 2% across the area of each of the petals.

11. The tampon applicator according to claim 1, wherein the insertion tip region and the inflection region form an insertion end, the insertion end including a radius of curvature generally defining an exterior geometry of the insertion end between the forward most end and a rearward most end where the inflection region meets the main body region, the radius of curvature exceeding about 0.400 inches.

12. The tampon applicator according to claim 1, wherein the termination of the slits form a tear-drop shape having a radius of curvature between about 0.028 inches and about 0.030 inches.

* * * * *